(12) United States Patent
Dalla Pria et al.

(10) Patent No.: US 8,382,850 B2
(45) Date of Patent: Feb. 26, 2013

(54) INSERT FOR ACETABULAR CUP

(75) Inventors: Paolo Dalla Pria, Udine (IT); Gabriele Lualdi, Fagagna (IT); Giacomo Marcuzzi, San Daniele Del Friuli (IT)

(73) Assignee: Limacorporate SpA, San Daniele del Friuli (UD) (IT)

( * ) Notice: Subject to any disclaimer, the term of this patent is extended or adjusted under 35 U.S.C. 154(b) by 356 days.

(21) Appl. No.: 12/601,443

(22) PCT Filed: May 23, 2008

(86) PCT No.: PCT/IB2008/001289
§ 371 (c)(1),
(2), (4) Date: May 24, 2010

(87) PCT Pub. No.: WO2008/146121
PCT Pub. Date: Dec. 4, 2008

(65) Prior Publication Data
US 2010/0234965 A1 Sep. 16, 2010

(30) Foreign Application Priority Data
May 25, 2007 (IT) .............................. UD2007A0088

(51) Int. Cl.
*A61F 2/32* (2006.01)
(52) U.S. Cl. ............... 623/22.28; 623/22.21; 623/22.24; 623/22.29

(58) Field of Classification Search ............... 623/22.11, 623/22.12, 22.15, 22.17, 22.18, 22.19, 22.2, 623/22.21, 22.24, 22.25, 22.27, 22.28, 22.29, 623/22.31, 22.32; *A61F 2/32*
See application file for complete search history.

(56) References Cited

U.S. PATENT DOCUMENTS

| 4,166,292 A * | 9/1979 | Bokros ..................... 623/21.18 |
| 5,156,626 A | 10/1992 | Broderick et al. |
| 6,797,007 B1 | 9/2004 | Von Chamier et al. |
| 2005/0246031 A1 * | 11/2005 | Frederick et al. ........... 623/22.29 |

FOREIGN PATENT DOCUMENTS

| DE | 198 13 074 A1 | 9/1999 |
| EP | 0 694 294 A1 | 1/1996 |
| EP | 1 733 705 A1 | 12/2006 |
| WO | 00/64383 A1 | 11/2000 |
| WO | 03/020180 A1 | 3/2003 |

* cited by examiner

*Primary Examiner* — David Isabella
*Assistant Examiner* — Yashita Sharma
(74) *Attorney, Agent, or Firm* — Novak Druce Connolly Bove + Quigg LLP

(57) ABSTRACT

An insert for an acetabular cup includes an insertion body having an external surface shaped to be able to be coupled with a mating seating of the acetabular cup. The insert includes at least a friction element positioned on the external surface to determine a predefined friction with the surface of the seating, so that, during use, the friction element prevents the relative rotation of the insertion body and the acetabular cup.

14 Claims, 3 Drawing Sheets

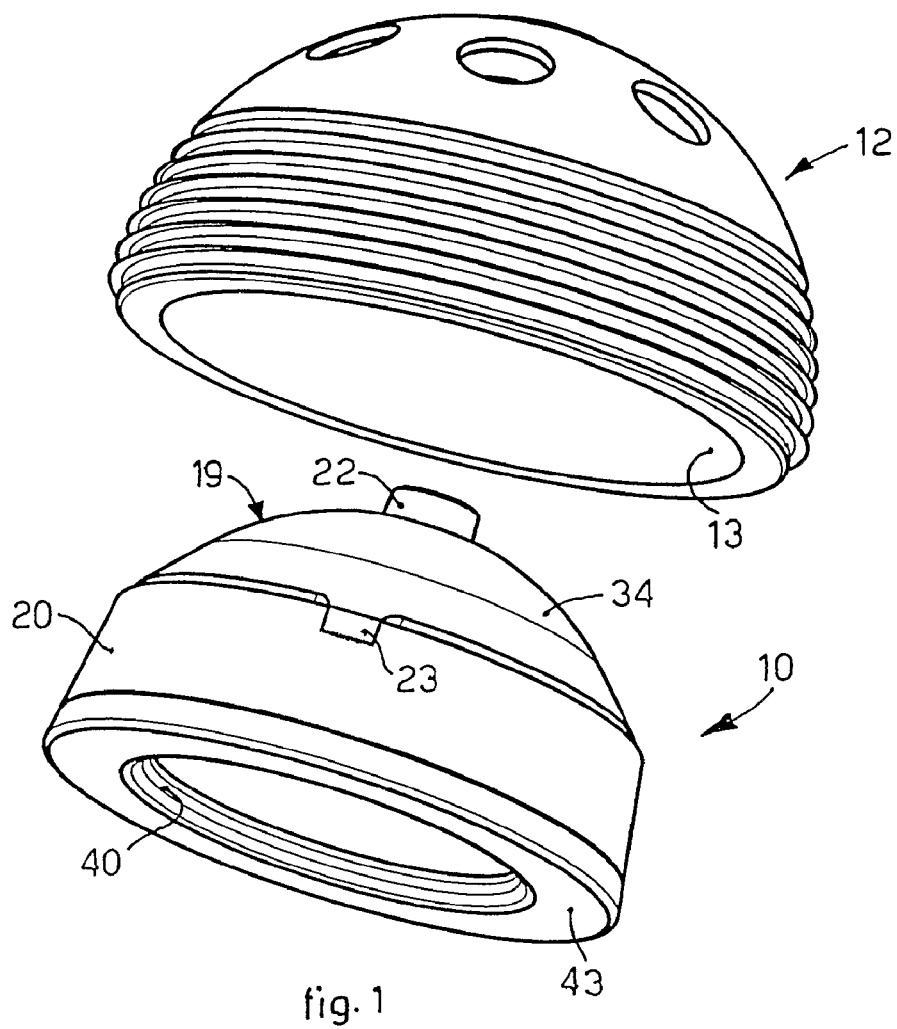
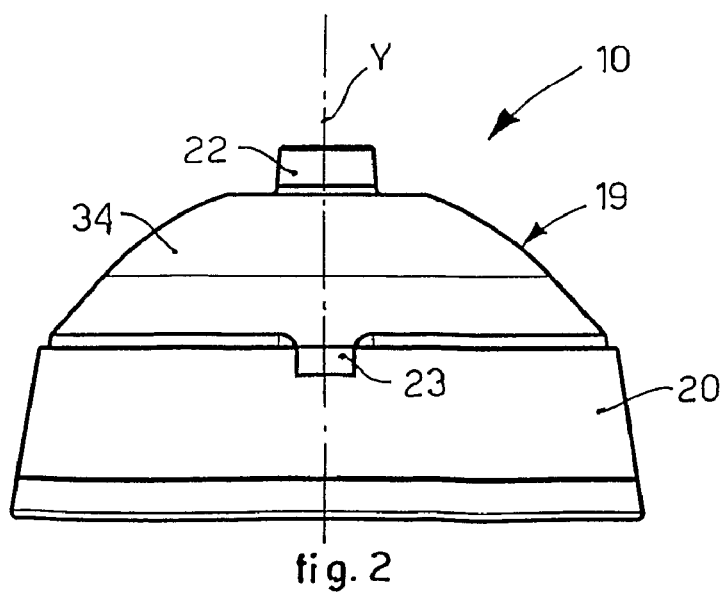

INSERT FOR ACETABULAR CUP

This application is a §371 National Stage Application of International Application No. PCT/IB2008/001289, filed on 23 May 2008, claiming the priority of Italian Patent Application No. UD2007A000088 filed on 25 May 2007.

FIELD OF THE INVENTION

The present invention concerns an insert able to be disposed inside the casing of an acetabular cup of the hip. The insert according to the present invention functions as a positioning and rotation seating for the head of a femoral prosthesis.

The invention also concerns a method for stabilizing the relative position of said insert and the relative acetabular cup in which the insert is applied.

BACKGROUND OF THE INVENTION

It is known, in the field of orthopedic prostheses, to make an insert with a semi-spherical cavity which functions as a positioning and rotation seating for the head of a femoral prosthesis.

The insert, in turn, is able to be disposed inside a mating casing or seating, shaped like a cone or truncated cone, made of osteo-compatible material, for example based on titanium or cobalt, of an acetabular cup of the hip. Both the insert and the acetabular cup are normally axial-symmetrical with respect to a common axis of symmetry.

The insert is usually made of cobalt-based metal, such as an alloy of cobalt-chrome-molybdenum, or of ceramic, or also of polyethylene, which is lighter and more economical.

In the case of polyethylene inserts, however, there may be an unwanted tendency to a relative rotation of the insert and the acetabular cup, with respect to the common axis of symmetry. This rotation between the insert and the acetabular cup is due both to the common circular geometry of the two components, and also to the difference in material of which they are made, since the acetabular cup is usually made of metal. Such rotation must absolutely be prevented, so as not to cause serious damage to the patient's articulation, such as dislocation or other.

This problem is found, however, every time there is a tendency to reciprocal rotation of the insert and the relative acetabular cup.

Purpose of the present invention is to achieve an insert that, once disposed in the casing of the acetabular cup, will maintain during normal use the position determined during the operation to insert the prosthesis and the acetabular cup, and that will not rotate with respect to the acetabular cup, and in particular will not rotate with respect to the common axis of symmetry.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purpose, according to the present invention an insert for an acetabular cup, provided with a seating, comprises an insertion body having an external surface able to be coupled with said seating of the acetabular cup.

According to a characteristic feature of the present invention, said insert comprises at least a friction element positioned, advantageously positioned fixed, on said external surface of the insertion body. The friction element is able to determine a predefined friction with the seating of the acetabular cup so that, during use, the friction element prevents the relative rotation of the insertion body and the seating and, consequently, between the insert and the acetabular cup with respect to the common axis of symmetry.

Therefore, the insert according to the present invention, once disposed in the acetabular cup, keeps, during normal use, the position determined during the operation of inserting the prosthesis and the acetabular cup.

Advantageously, the friction element is made of a material with a high friction coefficient. Even more advantageously, the friction element is made of the same material at least as the seating of the acetabular cup, for example a cobalt- or titanium-based alloy. In this way the general principle is effectively exploited according to which two equal materials on contact determine a high friction force which impedes and prevents their relative movement.

One advantageous possibility is that the friction element is attached to the insertion body releasably, in the sense that the friction element can be selectively mounted on and removed from the insertion body by means of a specific manual intervention by an operator, when the acetabular cup and the insert have not yet been implanted in the patient's hip. This is advantageous because it allows to sterilize the two components separately. Moreover, it allows to carry out assembly tests before implantation in the patient.

It is clear, however, that once the acetabular cup and the insert have been definitively implanted into the hip, the friction element can no longer be released from the insertion body.

Since a seating of an acetabular cup is typically shaped so as to have a circular cross section, advantageously shaped at least partly like a truncated cone, the insertion body too has at least a part shaped to mate with the seating.

A variant provides that said external surface of the insertion body has a first part shaped like a semi-spherical cap and a second part shaped like a truncated cone, on which the friction element is attached.

Another variant of the present invention provides that said external surface of the insertion body is shaped completely like a truncated cone, mating with the seating of the acetabular cup.

Both variants are advantageous, because they allow an effective conical coupling with the seating of the acetabular cup.

The present invention provides that the friction element can be disposed, according to contingent needs, on any portion whatsoever of the external surface of the insertion body and that, as well as a single friction element, several friction elements can also be provided.

An advantageous variant of the present invention provides that the friction element consists of a single ring, of a size coherent with that of the external surface of the insertion body.

An advantageous variant provides that, in this case, the friction element is formed by an annular wall with a shape compatible with that of the second part, and by a radial edge, protruding towards the inside of the friction element, which is able to cooperate with a corresponding annular seating, radially directed towards the inside, made along the same second part of the external surface of the insertion body.

To allow the solid clamping of the friction element and the insertion body, a suitable clamping means is provided which, according to a variant, consists of said radial edge of the friction ring, in cooperation with the annular seating of the insertion body.

Furthermore, to prevent the relative rotation of the friction element and the insertion body, it is provided to make, on the insertion body, a clamping means which is able to cooperate with the friction element or with a specific portion thereof.

A variant of the present invention provides to make a plurality of rings that function as friction elements.

Alternatively, or as an integration to the solutions described above, the present invention provides to make a plurality of friction elements, independent of each other, disposed along the external surface of the insertion body, which function as friction elements.

Advantageously, to achieve an effective impediment to the rotation around the common axis of the insertion body and the acetabular cup, the disposition of the friction element or friction elements is symmetrical with respect to said common axis and is coherent, for example circular, with the shape of the external surface of the insertion body and with the shape of the seating of the acetabular cup.

Furthermore, according to another variant, in order to have the greatest friction surface possible, the disposition of the friction element or friction elements is in substantial correspondence with the section of the external surface of the insertion body which corresponds to the greatest circular surface possible of said section, that is, in a substantial center line position, opposite the pole of the semi-spherical cap of the external surface of the insertion body.

The present invention also provides a method to stabilize the relative position between an insert for an acetabular cup and the acetabular cup itself, in which the acetabular cup is provided with a seating and in which the insert has an insertion body made of polymer material with an external surface shaped so as to be able to be coupled with said seating. The method according to the present invention comprises a first step in which a friction element is positioned, advantageously positioned fixed, on the external surface of the insertion body, the friction element being able to determine a predefined friction with said seating so that, during use, the friction element prevents the relative rotation between the insertion body and the seating itself, and a second step in which said external surface of the insertion body, bearing the friction element, is inserted and fixed in the seating of the acetabular cup.

BRIEF DESCRIPTION OF THE DRAWINGS

These and other characteristics of the present invention will become apparent from the following description of a preferential form of embodiment, given as a non-restrictive example with reference to the attached drawings wherein:

FIG. 1 is a perspective view of an insert according to the present invention and an acetabular cup with which the insert according to the present invention can be associated;

FIG. 2 is a front view of the insert in FIG. 1;

DETAILED DESCRIPTION OF A PREFERENTIAL FORM OF EMBODIMENT

Figure 3:
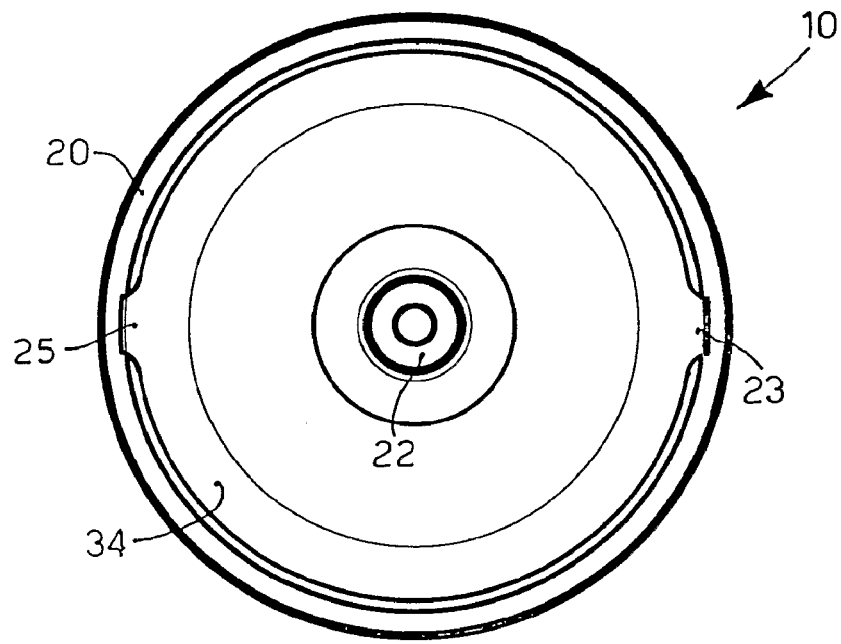
FIG. 3 is a plane view of the insert in FIG. 1.
Figure 4:
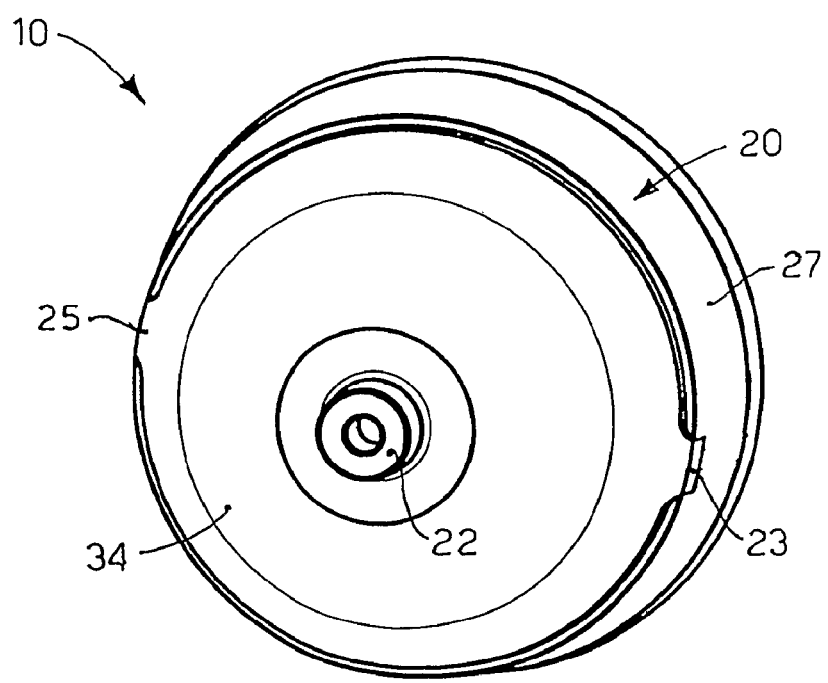
FIG. 4 is a perspective view of the insert in FIG. 1.

With reference to FIG. 1, an insert 10 according to the present invention is able to be inserted in an acetabular cup 12, in turn housed in a relative acetabular seating, not shown in the drawings, of the hip bone. The acetabular cup 12 is of the traditional type, for example made of a cobalt- or titanium-based alloy, with a seating 13 at least partly shaped like a truncated cone, which is able to receive the insert 10.

Figure 6:
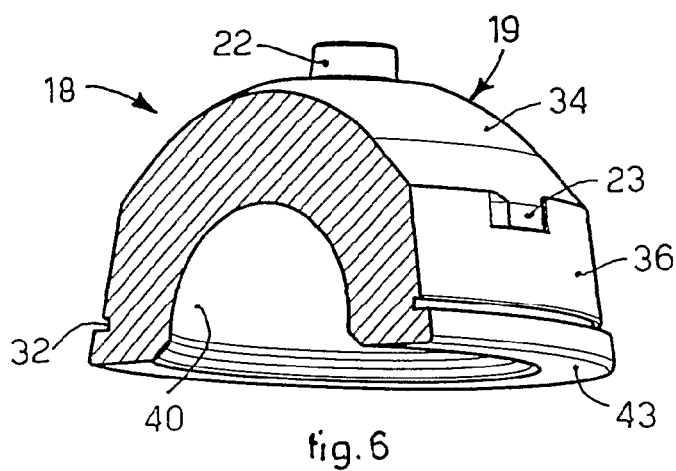
FIG. 6 is a perspective view of a part of the insert in FIG. 1.

The insert 10 is formed by an insertion body 18, shown in detail in FIG. 6, axial-symmetrical with respect to an axis of symmetry Y and normally made of polyethylene, preferably of the UHMWPE type (Ultra High Molecular Weight Polyethylene).

It is clear that other suitable polymer materials can be used apart from UHMWPE, such as polyethylethyleneketone (PEEK).

The body 18 has both an external surface 19, which is inserted into the seating 13, and also an internal cavity 40 (FIGS. 1, 5 and 6), inside which a prosthetic head, not shown in the drawings, can be inserted. An annular portion 43 connects the external surface 19 with the inside of the cavity 40.

Figure 5:
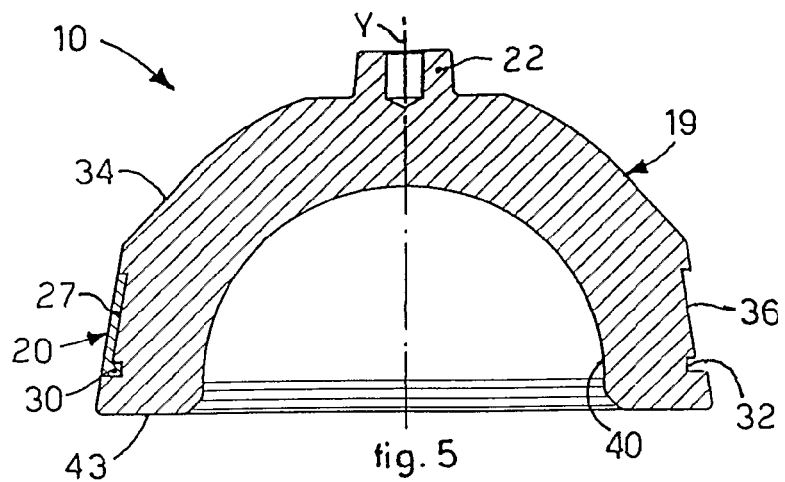
FIG. 5 is a section of the insert in FIG. 1.

In particular, the external surface 19 is formed by a semi-spherical cap part 34, of a shape mating with said seating 13, and a truncated cone part 36, provided below the cap part 34 and coaxial therewith (FIGS. 5 and 6).

A variant, not shown in the drawings, provides that the external surface 19 is shaped completely like a truncated cone.

In particular, in correspondence with the angular position of the pole of the cap part 34, and coaxial to the axis Y, a centering pin 22 is made (FIGS. 1-6) for coupling, in a known manner, with the acetabular cup 12.

Figure 7:
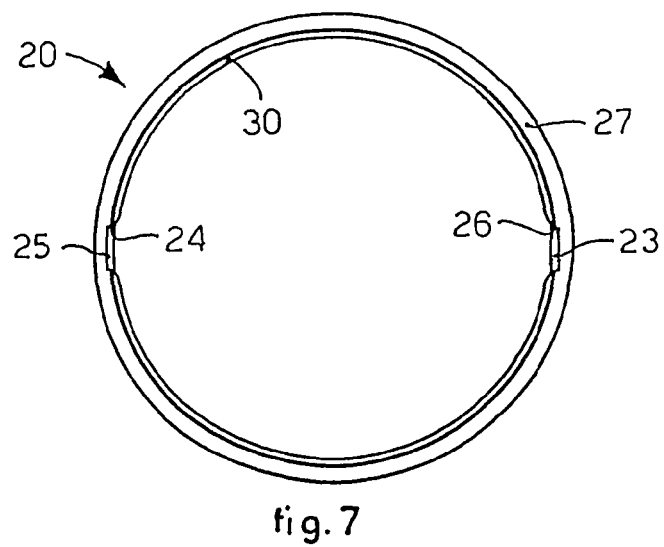
FIG. 7 is a plane view of another part of the insert in FIG. 2.

The insert 10 comprises a ring 20, shown in detail in FIG. 7, made from a sheet advantageously made of a metal, for example a cobalt- or titanium-based alloy, the same as the one used to make the acetabular cup 12. In this way, the ring 20 is able to determine a predefined friction between the insert 10 and the seating 13, to prevent the reciprocal rotation between these two components with respect to the axis Y. Advantageously, in fact, the choice of making the ring 20 of the same material as that of the acetabular cup 12 allows to obtain optimum friction between the two components.

The ring 20 can have an aperture (not shown) which can allow the ring 20 to deform slightly and elastically, opening and closing it, in order to position it on the truncated cone part 36 (FIGS. 2 and 8).

Once positioned outside on the body 18, possibly forcing it to slide on the truncated cone external surface 19, the ring 20, thanks to its elastic properties, is disposed to closely surround the truncated cone part 36.

Advantageously, the ring 20 has an L-shaped cross section, as can be seen in FIG. 5, formed by an annular wall 27 able to surround the truncated cone part 36 and by a radial edge 30 disposed at the lower part.

The edge 30 is inserted into a corresponding annular seating or undercut 32, made along the truncated cone part 36, at the lower or upper part, according to needs, so as to determine the axial retention of the ring 20 with respect to the body 18 and to define a solid combination of these two components.

Furthermore, to prevent the reciprocal rotation around the axis Y of the body 18 and the ring 20, at least a block 23, 25 is provided, advantageously two, on the truncated cone part 36, which act as abutment elements to prevent the rotation of the ring 20. In particular, the blocks 23 and 25 are able to cooperate with corresponding hollows 24 and 26 made in the ring 20. The hollows 24 and 26 are advantageously provided in diametrically opposite positions and have a length substantially equal to the length of the blocks 23 and 25, so as to clamp the rotation of the ring 20.

A variant, not shown in the drawings, provides that the hollows 24 and 26 are made instead in the truncated cone part 36 and that the blocks 23 and 25 are made at the ends of the ring 20, in an equivalent manner to that described above.

It is clear that modifications and/or additions of parts may be made to the insert for an acetabular cup as described heretofore, without departing from the field and scope of the present invention.

It is also clear that, although the present invention has been described with reference to some specific examples, a person of skill in the art shall certainly be able to achieve many other equivalent forms of insert for an acetabular cup, having the characteristics as set forth in the claims and hence all coming within the field of protection defined thereby.

The invention claimed is:

1. An insert for an acetabular cup comprising an insertion body having an external surface shaped to be able to be coupled with a mating seating of said acetabular cup,
   the insert comprising;
   at least a friction element which is positioned on said external surface and is able to determine a predefined friction with the surface of said seating, so that, during use, said friction element prevents the relative rotation of said insertion body and said acetabular cup, wherein said friction element is positioned fixed on said external surface,
   first clamping means able to keep the friction element solid with the insertion body,
   wherein said external surface comprises at least a part, shaped for mating with said seating, with which said friction element is associated, wherein the first clamping means comprises a radial edge disposed transverse to an annular wall of said friction element, and a corresponding annular seating, made on said part, able to cooperate with the radial edge.

2. The insert as in claim 1, wherein said part is shaped like a truncated cone.

3. The insert as in claim 1, wherein said friction element is shaped like a ring, with a size compatible with said part of said external surface.

4. The insert as in claim 1, comprising second clamping means able to prevent the reciprocal rotation of said friction element and said insertion body.

5. The insert as in claim 1, comprising second clamping means able to prevent the reciprocal rotation of said friction element and said insertion body, wherein said second clamping means comprises at least a hollow, made on said annular wall of said friction element, and at least a corresponding block protruding from said part and able to cooperate with the hollow.

6. The insert as in claim 1, comprising second clamping means able to prevent the reciprocal rotation of said friction element and said insertion body, wherein said second clamping means comprises at least a block protruding from said annular wall of said friction element, and at least a corresponding hollow made on said part and able to cooperate with the block.

7. The insert as in claim 1, wherein said insertion body is made of a polymer material.

8. The insert as in claim 1, wherein said friction element is made of the same material of which at least said seating of said acetabular cup is made.

9. The insert as in claim 8, wherein said friction element is made of metal material.

10. The insert as in claim 9, wherein said metal material is titanium-based.

11. The insert as in claim 9, wherein said metal material is cobalt-based.

12. The insert as in claim 1, wherein said seating is shaped to allow the fixed positioning of said friction element.

13. A method to stabilize the relative position of an insert of claim 1 for an acetabular cup and said acetabular cup, wherein said acetabular cup is provided with a seating and wherein said insert has an insertion body with an external surface shaped to be able to be coupled with said seating,
    the insert comprising:
    at least a friction element which is positioned on said external surface and is able to determine a predefined friction with the surface of said seating, so that, during use, said friction element prevents the relative rotation of said insertion body and said acetabular cup, wherein said friction element is positioned fixed on said external surface,
    first clamping means able to keep the friction element solid with the insertion body,
    wherein said external surface comprises at least a part, shaped for mating with said seating, with which said friction element is associated, wherein the first clamping means comprises a radial edge disposed transverse to an annular wall of said friction element, and a corresponding annular seating, made on said part, able to cooperate with the radial edge
    comprising the following steps:
    a first step comprising positioning the friction element on said external surface, said friction element being able to determine a predefined friction with said seating, so that, during use, said friction element prevents the relative rotation of said insertion body and said acetabular cup; and
    a second step comprising positioning said insertion body, bearing said friction element, in said seating of said acetabular cup.

14. The insert as in claim 1, wherein said insertion body is made of polyethylene.

* * * * *